United States Patent
Drake

(10) Patent No.: US 10,493,115 B2
(45) Date of Patent: Dec. 3, 2019

(54) EXTRACT FOR TREATING SKIN CONDITIONS

(71) Applicant: Karen Drake, Bel Air, CA (US)

(72) Inventor: Karen Drake, Bel Air, CA (US)

( * ) Notice: Subject to any disclaimer, the term of this patent is extended or adjusted under 35 U.S.C. 154(b) by 293 days.

(21) Appl. No.: 15/331,679

(22) Filed: Oct. 21, 2016

(65) Prior Publication Data

US 2018/0110815 A1    Apr. 26, 2018

(51) Int. Cl.
| | |
|---|---|
| *A61K 36/185* | (2006.01) |
| *A61K 36/15* | (2006.01) |
| *A61K 47/10* | (2017.01) |
| *A61K 47/12* | (2006.01) |
| *A61K 47/22* | (2006.01) |
| *A61K 9/06* | (2006.01) |
| *A61P 31/04* | (2006.01) |
| *A61P 17/10* | (2006.01) |
| *A61P 17/00* | (2006.01) |
| *A61K 36/886* | (2006.01) |

(52) U.S. Cl.
CPC .............. *A61K 36/185* (2013.01); *A61K 9/06* (2013.01); *A61K 36/15* (2013.01); *A61K 47/10* (2013.01); *A61K 47/12* (2013.01); *A61K 47/22* (2013.01); *A61P 17/00* (2018.01); *A61P 17/10* (2018.01); *A61P 31/04* (2018.01); *A61K 36/886* (2013.01); *A61K 2236/00* (2013.01); *A61K 2236/15* (2013.01); *A61K 2236/30* (2013.01); *A61K 2236/33* (2013.01); *A61K 2236/39* (2013.01)

(58) Field of Classification Search
None
See application file for complete search history.

(56) References Cited

U.S. PATENT DOCUMENTS

| | | | |
|---|---|---|---|
| 2005/0014730 A1* | 1/2005 | Carlson | A61K 31/56 514/169 |
| 2005/0181073 A1 | 8/2005 | Vana | |
| 2006/0182708 A1 | 8/2006 | Bockmuhl et al. | |
| 2009/0208593 A1* | 8/2009 | Zannini | A61K 36/00 424/725 |
| 2010/0210702 A1* | 8/2010 | Vontz | A61K 31/4178 514/397 |
| 2015/0093346 A1 | 4/2015 | Burke-Colvin et al. | |
| 2015/0374769 A1 | 12/2015 | Hines et al. | |

FOREIGN PATENT DOCUMENTS

WO    WO 2012/126983 A1    10/2012

\* cited by examiner

*Primary Examiner* — Terry A McKelvey
*Assistant Examiner* — Catheryne Chen
(74) *Attorney, Agent, or Firm* — Plager Schack LLP; Mark H. Plager; Kara Verryt

(57) ABSTRACT

Some embodiments of the present disclosure include a therapeutic extract for selectively treating skin disorders, such as acne and rosacea. The therapeutic extract may include glycerin; water, such as reverse osmosis water; blackcurrant; pine; gluconolactone; citric acid; and sodium benzoate. In embodiments, the blackcurrant may be organic ribes nigrum and may be derived from fruit of a blackcurrant plant. Moreover, the pine may be *pinus* spp and may be derived from a needle of a pine plant.

11 Claims, No Drawings

EXTRACT FOR TREATING SKIN CONDITIONS

BACKGROUND

The embodiments herein relate generally to skin treatment compositions, and more particularly, to an extract composition for treating skin conditions, such as topical acne and rosacea.

Acne affects about 80% of Americans at some point in their lives. However, scientists know little about what causes the disorder and have made limited progress in developing new strategies for treating it. Dermatologists' arsenal of anti-acne tools, including benzoyl peroxide, antibiotics, and Accutane (isotretinoin), has not expanded in decades. Moreover, most severe cases of acne do not respond to antibiotics, and Accutane can produce serious side effects.

Antibiotics may not work for treating acne due to the phenomenon of antibiotic resistance, where individual bacteria develop resistance to an antibiotic by sheer random mutation. Most mutations kill bacteria so that they do not reproduce and pass the mutation to their progeny. However, some mutations give a single bacterium the ability to resist a medication.

An individual bacterium generally is not a problem. However, bacteria can reproduce as often as every 20 minutes, and bacteria have the ability to swap genetic material through a process called horizontal gene transfer. A bacterium can share its mutation with its neighbors by direct transfer of DNA. Thus, one resistant bacterium can become millions or billions and can spread from person to person, unhindered by treatment with the antibiotic to which it has acquired resistance.

When it comes to acne, doctors prescribe the medication, and acne sufferers tend to use it until their skin looks better, but not necessarily until all the bacteria are killed. Thus, the antibiotic just wipes out the most susceptible bacteria and leaves the resistant bacteria. When the patient stops taking the antibiotic, the resistant bacteria are free to multiply unchecked by competition from other microbes, and acne can actually come back worse than it was before treatment.

Acne bacteria have become resistant to many antibiotics, including Rifampin (to which 17% of acne bacteria are resistant), Tetracycline (to which 35% of acne bacteria are resistant), Amoxicillin (to which 40% of acne bacteria are resistant), Clindamycin (to which 50% of acne bacteria are resistant), Erythromycin (to which 52% of acne bacteria are resistant), Neomycin (to which 80% of acne bacteria are resistant), and Cloxacillin (to which 100% of acne bacteria are resistant).

While antibiotic resistance is a problem in treating acne, it is not the only issue. There is emerging evidence that the old idea that just one strain of bacteria, *Propionibacterium acnes*, causes acne is wrong. Acne experts in Asia are finding *Staphylococcus aureus* in pimples. However, the experts do not know whether the reason staph bacteria seem to contribute to acne in Asia has to do with Asian skin or Asian weather. This means, at least in Asia, at least two kinds of acne bacteria need to be controlled and that getting rid of one bacterium without getting rid of the second bacterium may just allow one strain to grow unchecked. It also means that impetigo, a staph infection that grows in cuts in the skin, may aggravate acne, which occurs in pores, and vice versa.

Because of the issues with antibiotics, more and more dermatologists are recommending that antibiotics should be just one part of acne treatment. Most skin doctors recommend using benzoyl peroxide to get rid of bacteria that antibiotics miss, but benzoyl peroxide comes with its own issues. For instance, benzoyl peroxide has been found to be very irritating for dry and sensitive skin types, and allergic reactions are extremely common. There is also compelling scientific data that shows that benzoyl peroxide users may age faster due to free radicals being formed during the manufacture of the benzoyl peroxide. Specifically, benzoyl peroxide is usually prepared by treating hydrogen peroxide with benzoyl chloride. Because the oxygen-oxygen bond in peroxides is weak, the benzoyl peroxide readily undergoes hemolysis (symmetrical fusion), forming free radicals.

Free radicals have strong bactericidal activity that works to kill any present bacteria, including both the bad bacteria forming the acne and any good bacteria that may be present on the skin. While benzoyl peroxide is not mutagenic, the Department of Environmental Health Sciences, John Hopkins Medical Institutions has found that benzoyl peroxide has been observed to produce strand breaks in DNA of exposed cells. Harvard Medical School and Wellman Laboratories of Photomedicine at Massachusetts General Hospital have published studies showing repeated chronic treatment with benzoyl peroxide caused changes that resemble those caused by low fluence UVB, which suggests that common inflammatory mechanisms may be involved in the production of the changes seen with chronic UVB or benzoyl peroxide exposure. The findings further support that oxidative stress plays a role in the photo aging process. Thus, while benzoyl peroxide may be beneficial for treating acne, it also breaks down the skin, accelerates aging, and compromises skin health.

Retinoids may also be prescribed to treat acne either in combination with benzoyl peroxide or on their own; however, use of retinoids is also fraught with side effects. Specifically, topical retinoids often cause a retinoid reaction characterized by itching, burning, reddening, and peeling. Retinoid use also causes photosensitization and may also cause teratogenicity or embryotoxicity in pregnant women if used systemically.

Therefore, what is needed is an extract composition that selectively suppresses bad bacteria that causes the skin disorders, while simultaneously enhancing good bacteria present on the skin, resulting in limited side effects and an enhanced skin microbiome.

SUMMARY

Some embodiments of the present disclosure include a therapeutic extract for selectively treating skin disorders, such as acne and rosacea. The therapeutic extract may include glycerin; water, such as reverse osmosis water; blackcurrant; pine; gluconolactone; citric acid; and sodium benzoate. In embodiments, the blackcurrant may be organic ribes nigrum and may be derived from fruit of a blackcurrant plant. Moreover, the pine may be *pinus* spp and may be derived from a needle of a pine plant.

DETAILED DESCRIPTION OF CERTAIN EMBODIMENTS

In the following detailed description of the invention, numerous details, examples, and embodiments of the invention are described. However, it will be clear and apparent to one skilled in the art that the invention is not limited to the embodiments set forth and that the invention can be adapted for any of several applications.

The extract composition of the present disclosure may be used to prevent or treat skin disorders, such as acne, rosacea, staph infections, and the like and comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

1. Glycerin
2. Water
3. Blackcurrant
4. Pine
5. Gluconolactone
6. Citric Acid
7. Sodium Benzoate The various elements of the composition of the present disclosure may be related in the following exemplary fashion. It is not intended to limit the scope or nature of the relationships between the various elements and the following examples are presented as illustrative examples only.

By way of example, some embodiments of the present disclosure include a therapeutic extract for treating skin disorders, such as acne and rosacea, the therapeutic extract comprising glycerin, water, blackcurrant, pine, gluconolactone (D-Glcono-1,5-lactone), citric acid, and sodium benzoate. In embodiments, the blackcurrant may comprise organic ribes nigrum and may be derived from the fruit of the plant, while the pine may comprise organic *pinus* spp and may be derived from the needle of the plant. In some embodiments, the therapeutic extract may comprise from about 15 to about 40 wt %, such as about 30 wt %, glycerin; from about 20 to about 30 wt %, such as about 29.2 wt %, water; from about 10 to about 30 wt %, such as about 20 wt %, blackcurrant; from about 10 to about 30 wt %, such as about 20 wt %, pine; from about 0.10 to about 1.00 wt %, such as about 0.45 wt %, gluconolactone; from about 0.10 to about 0.50 wt %, such as about 0.2 wt % citric acid; and from about 0.10 to about 0.20 wt %, such as about 0.15 wt %, sodium benzoate, based on a total weight of the extract. In particular embodiments, the amount of blackcurrant may be equal to the amount of pine.

The therapeutic extract of the present disclosure may be made using a multiple step method. The method may include preparing the dry botanicals; preparing the extraction solvent; extracting the blackcurrant and the pine, creating the therapeutic extract; pasteurizing the therapeutic extract; preserving the therapeutic extract; and packaging the therapeutic extract.

Preparing the dry botanicals may be referred to herein as Stage A. Stage A may comprise receiving the dry herbs in whole form. The dry herbs may be divided into a first half and a second half, wherein the first half is put through a high-speed electric grinder mill at a speed of, for example, about 32000 r/min, to produce a rough crush level. The second half may be left whole. The dry rough mix and the second half may be placed into a mixing vessel, such as a large stainless steel mixing vessel, and blended for about 15 minutes prior to being steeped into an extraction solvent.

Preparing the extraction solvent may be referred to herein as Stage B. Stage B may comprise mixing water, such as 90% reverse osmosis water, with aloe vera juice, such as 10% organic whole leave aloe vera juice, in a mixing vessel, such as a stainless steel mixing vessel separate from that used in Stage A. The water and *aloe vera* juice may be mixed for about 10 minutes without any heat. Glycerin, such as pure organic vegetable glycerin, may be added to the vessel and mixed for an additional about 10 minutes, creating the extraction solvent. Up to about 30% glycerin may be added during this step.

The extraction process may include multiple steps, referred to herein as Stage C, Stage D, and Stage E. Stage C may comprise slowly introducing the extraction solvent into the mixing vessel from Stage A, completely covering the dry mix. The vessel may then be closed and left for about 48 hours. During the first 24 hours of extraction, the plant material (i.e., the dry mix) may absorb liquid. Thus, the vessel may be checked to ensure that the dry mix is completely covered in solvent. Additional solvent may be added, if necessary, and the mixture may be agitated for up to about 15 minutes.

After 48 hours, Stage D may occur. Stage D may include squeezing the extract through a heavy mechanical press, removing all or almost all of the liquid matter. The press is so heavy that the spent material may be left completely dry. The dry material may be, for example, used as compost.

After the separation of the liquid matter and dry material, Stage E may occur. During Stage E, the extract (the liquid matter) may go through a micro-filtration process down to about 0.2 microns, helping to remove pathogens and particle matter, leaving a crystal clear, light pink liquid extract. The micro-filtration (MF) process may help remove plant sedimentation and many micro-organisms from the water, such as micro-organisms that are invisible to the naked eye but greater than 0.2 microns in diameter. Rejected particles, including plant pathogen spores, may be removed periodically to waste by an automated compressed air backwash, which may allow for sterilization of the water without the use of additional chemicals. Although many micro-organisms are removed, viruses may sometimes remain in the water and, thus, after extraction, pasteurization may occur.

After extraction, pasteurization may occur. Pasteurization may be referred to herein as Stage F. Stage F may include heating the extract to about 80° F. for about 10 minutes to remove any remaining pathogens. The extract may then be left to completely cool.

After the extract has been pasteurized, it may be preserved, which may be referred to herein as Stage G. Stage G may include adding preservatives, such as gluconolactone and sodium benzoate, to the extract. The pH of the extract may be adjusted to be within a range of from about 4.6 to about 5. The pH may be adjusted by adding citric acid, as needed.

After the extract has been preserved, packaging may occur. This may be referred to as Stage H. Stage H may include filling containers, such as high-density polyethylene (HDPE) jerry cans in a high care area where the extract may be micro-tested for a final time to ensure that the extract is completely devoid of pathogens. As used herein, a high care area may refer to an area designed to a high standard where practices relating to personnel, ingredients, equipment, packaging, and environment aim to minimize product contamination by pathogenic micro-organisms.

As mentioned above, the therapeutic extract of the present disclosure may be used to treat skin conditions, such as acne. Specifically, the therapeutic extract may selectively suppress *p. acnes* and *staph aureus*, which are acne-causing bacteria, without suppressing any of the skin's good bacteria. For example, in embodiments, the therapeutic extract may be mixed with other ingredients to form a cream for treating acne. Examples of such creams are explained below.

EXPERIMENTAL RESULTS

Example 1

Composition vs. *Propionibacterium Acnes*

*Propionibacterium acnes* (*P. Acnes*) was prepared by inoculating the surface of TSA slants. Each microorganism was then incubated at 30° C. to 35° C. for 18 to 24 hours. Following the incubation period, the slants were washed with sterile Serological Saline Solution to harvest the microorganisms. Using Culti-Loops, microorganisms were grown and adjusted to $10^6$ colony forming units (cfu) per mL and used as a stock suspension. An additional 1:10 dilution of the stock suspension was made using Serological Saline Solution to achieve a concentration of approximately $10^7$ cfu per mL.

For the microorganism to be tested, 20 mL of the test product (the composition comprising 79.65 wt % water, 10 wt % organic blackcurrant, 10 wt % organic pine, 15 wt % gluconolactone and sodium benzoate, and 0.2% citric acid) and 20 mL of Serological Saline Solution was added into separate sterile tubes. Each 20 mL sample of test product and Serological Saline Solution was inoculated with 0.2 mL of the $10^7$ cfu/mL suspensions. These inoculums resulted in approximately $10^6$ cfu/mL into the test product and Serological Saline Solution control.

At the time intervals of 30 seconds, 1 minute, 5 minutes, 30 minutes, and 60 minutes, 1.0 mL from the inoculated test product was taken and placed into 9.0 mL of Modified Letheen Broth (1:10 dilution). Additional 1:10 serial dilutions were prepared using neutralizing broth to achieve 1:100 and 1:1000 dilutions.

1 mL from each dilution was plated in sterile Petri dishes, and melted TSA agar was added as the growth medium for bacterial organisms.

The bacterial plates were incubated at 30° C. to 35° C. for 48 hours. The same procedure was repeated for the Serological Saline Solution control. After the incubation period. All plates were counted to determine the number of microorganisms remaining at the various time points.

Results:

| Exposure Time | Concentration of Organism (CFU/mL) | | % Reduction | | Log Reduction | |
|---|---|---|---|---|---|---|
| | Control | Product | Control | Product | Control | Product |
| INITIAL | $5.60 \times 10^6$ | | | | | |
| 30 sec | $5.60 \times 10^6$ | $1.30 \times 10^6$ cfu/gm/ml | N/A | 76.78% | 0.00 | 0.63 |
| 1 min | $5.60 \times 10^6$ | $1.20 \times 10^6$ cfu/gm/ml | N/A | 78.57% | 0.00 | 0.67 |
| 5 min | $5.60 \times 10^6$ | $1.10 \times 10^6$ cfu/gm/ml | N/A | 80.35% | 0.00 | 0.70 |
| 30 min | $5.60 \times 10^6$ | $4.50 \times 10^3$ cfu/gm/ml | N/A | 99.91% | 0.00 | 3.09 |
| 60 min | $1.40 \times 10^6$ | <10 cfu/gm/ml | 75.00% | 99.99% | 0.60 | N/A |

Data Calculation: The concentration of each microorganism for the control and product is listed for each interval. These numbers are expressed in terms of scientific notation. The next two headings represent the "% Reduction" and "Log Reduction" information for each time point. Both calculations are used to express the change (reduction or increase) of the microorganism population relative to starting inoculums.

$$\% \text{ Reduction} = \frac{\text{Initial Count} - \text{Count at} \times \text{time interval}}{\text{Initial Count}} \times 100$$

For example, % Reduction for Control:

$$\% \text{ Reduction} = \frac{5.6 \times 10^6 - 1.40 \times 10^6}{5.6 \times 10^6} \times 100$$

The Log Reduction is calculated as follows:

Log Reduction=$\log_{10}$(initial count)−$\log_{10}$(×times interval)

For example, Log Reduction for Control:

Log Reduction=$\log_{10}(5.6 \times 10^6) - \log_{10}(1.40 \times 10^6)$= 6.74−6.14=0.60 log reduction Discussion: The minimum bactericidal concentration is defined as 99.9% decrease (3 log) in the initial inoculums. The test product had no counts for growth when exposed to *P. acnes* after 30 minutes.

Conclusion: The results indicate that the test product has 99.9% log reduction for *P. acnes* at 30 minutes of contact time.

Example 2

Composition Plus Salicylic Acid vs. *Staphylococcus aureus* (Methicillin Resistant *Staphylococcus aureus*)

*Staphylococcus aureus* (Methicillin Resistant *Staphylococcus aureus*) was prepared by inoculating the surface of TSA slants. Each microorganism was then incubated at 30° C. to 35° C. for 18 to 24 hours. Following the incubation period, the slants were washed with sterile Serological Saline Solution to harvest the microorganisms. Using Culti-Loops, microorganisms were grown and adjusted to $10^8$ cfu/mL and used as a stock suspension. An additional 1:10 dilution of the stock suspension was made using Serological Saline Solution to achieve a concentration of approximately $10^7$ cfu/mL.

For the microorganism to be tested, 20 mL of the test product and 20 mL of the Serological Saline Solution were added into separate sterile tubes. Each 20 mL sample of test product and Serological Saline Solution was inoculated with 0.2 mL of the $10^7$ cfu/mL suspensions. These inoculums resulted in approximately $10^6$ cfu/mL into the product and into the Serological Saline Solution control.

At time intervals of 30 seconds, 1 minute, 5 minutes, 30 minutes, and 60 minutes, 1.0 mL from the inoculated test product was taken and placed into 9.0 mL of modified letheen broth (1:10 dilution). Additional 1:10 serial dilutions were prepared using neutralizing broth to achieve 1:100 and 1:1000 dilutions.

1 mL from each dilution was plated in sterile Petri dishes, and melted TSA agar was added as the growth medium for bacterial organisms. The bacterial plates were incubated at 30° C. to 35° C. for 48 hours. The same procedure was repeated for the Serological Saline Solution control. After the incubation period, all plates were counted to determine the number of microorganisms remaining at the various time points.

Results:

| Exposure Time | Concentration of Organism (cfu/mL) | | % Reduction | | Log Reduction | |
|---|---|---|---|---|---|---|
| | Control | Product | Control | Product | Control | Product |
| Initial | $2.30 \times 10^6$ | | | | | |
| 30 sec | $2.30 \times 10^6$ | <10 cfu/g/mL | N/A | 99.99% | 0.00 | N/A |
| 1 min | $2.30 \times 10^6$ | <10 cfu/g/mL | N/A | 99.99% | 0.00 | N/A |
| 5 min | $2.30 \times 10^6$ | <10 cfu/g/mL | N/A | 99.99% | 0.00 | N/A |
| 30 min | $2.30 \times 10^6$ | <10 cfu/g/mL | N/A | 99.99% | 0.00 | N/A |
| 60 min | $1.20 \times 10^6$ | <10 cfu/g/mL | 47.82% | 99.99% | 0.29 | N/A |

Data calculation was performed the same way as described above in Example 1.

Discussion: The minimum bactericidal concentration is defined as 99.9% decrease (3 log) in the initial inoculums. The test product had no counts for growth when exposed to *Staphylococcus aureus* (Methicillin Resistant *Staphylococcus aureus*) after 30 seconds.

Conclusion: The results indicate that the test product with 1% salicylic acid has 99.9% log reduction for *Staphylococcus aureus* (Methicillin Resistant *Staphylococcus aureus*) at 30 seconds of contact time.

Example 3

Composition (in Serum form) vs. *Propionibacterium Acnes*

*Propionibacterium acnes* (*P. Acnes*) was prepared by inoculating the surface of TSA slants. Each microorganism was then incubated at 30° C. to 35° C. for 18 to 24 hours. Following the incubation period, the slants were washed with sterile Serological Saline Solution to harvest the microorganisms. Using Culti-Loops, microorganisms were grown and adjusted to $10^6$ colony forming units (cfu) per mL and used as a stock suspension. An additional 1:10 dilution of the stock suspension was made using Serological Saline Solution to achieve a concentration of approximately $10^7$ cfu per mL.

For the microorganism to be tested, 20 mL of the test product in serum form (the composition comprising 79.65 wt % water, 10 wt % organic blackcurrant, 10 wt % organic pine, 15 wt % gluconolactone and sodium benzoate, and 0.2% citric acid) and 20 mL of Serological Saline Solution was added into separate sterile tubes. Each 20 mL sample of test product and Serological Saline Solution was inoculated with 0.2 mL of the $10^7$ cfu/mL suspensions. These inoculums resulted in approximately $10^6$ cfu/mL into the test product and Serological Saline Solution control.

At the time intervals of 30 seconds, 1 minute, 5 minutes, 30 minutes, and 60 minutes, 1.0 mL from the inoculated test product was taken and placed into 9.0 mL of Modified Letheen Broth (1:10 dilution). Additional 1:10 serial dilutions were prepared using neutralizing broth to achieve 1:100 and 1:1000 dilutions.

1 mL from each dilution was plated in sterile Petri dishes, and melted TSA agar was added as the growth medium for bacterial organisms.

The bacterial plates were incubated at 30° C. to 35° C. for 48 hours. The same procedure was repeated for the Serological Saline Solution control. After the incubation period. All plates were counted to determine the number of microorganisms remaining at the various time points.

Results:

| Exposure Time | Concentration of Organism (CFU/mL) | | % Reduction | | Log Reduction | |
|---|---|---|---|---|---|---|
| | Control | Product | Control | Product | Control | Product |
| INITIAL | $1.70 \times 10^7$ | | | | | |
| 30 sec | $1.70 \times 10^7$ | $1.80 \times 10^6$ cfu/gm/ml | N/A | 89.41% | 0.00 | 0.98 |
| 1 min | $1.70 \times 10^7$ | $2.00 \times 10^5$ cfu/gm/ml | N/A | 98.82% | 0.00 | 1.93 |
| 5 min | $1.70 \times 10^7$ | $4.10 \times 10^4$ cfu/gm/ml | N/A | 99.75% | 0.00 | 2.62 |
| 30 min | $1.70 \times 10^7$ | $1.00 \times 10^3$ cfu/gm/ml | N/A | 99.99% | 0.00 | 4.23 |
| 60 min | $3.60 \times 10^6$ | <10 cfu/gm/ml | 78.82% | 99.99% | 0.68 | N/A |

Data Calculation was performed the same way as described above in Example 1.

Discussion: The minimum bactericidal concentration is defined as 99.9% decrease (3 log) in the initial inoculums. The test product had no counts for growth when exposed to *P. acnes* after 30 minutes.

Conclusion: The results indicate that the test product (in Serum form) has 99.9% log reduction for *P. acnes* at 30 minutes of contact time.

Example 4

Composition vs. *Staphylococcus Aureus*

*Staphylococcus aureus* was prepared by inoculating the surface of TSA slants. Each microorganism was then incubated at 30° C. to 35° C. for 18 to 24 hours. Following the incubation period, the slants were washed with sterile Serological Saline Solution to harvest the microorganisms. Using Culti-Loops, microorganisms were grown and adjusted to $10^6$ colony forming units (cfu) per mL and used as a stock suspension. An additional 1:10 dilution of the stock suspension was made using Serological Saline Solution to achieve a concentration of approximately $10^7$ cfu per mL.

For the microorganism to be tested, 20 mL of the test product (the composition comprising 79.65 wt % water, 10 wt % organic blackcurrant, 10 wt % organic pine, 15 wt % gluconolactone and sodium benzoate, and 0.2% citric acid) and 20 mL of Serological Saline Solution was added into separate sterile tubes. Each 20 mL sample of test product and Serological Saline Solution was inoculated with 0.2 mL of the $10^7$ cfu/mL suspensions. These inoculums resulted in approximately $10^6$ cfu/mL into the test product and Serological Saline Solution control.

At the time intervals of 30 seconds, 1 minute, 5 minutes, 30 minutes, and 60 minutes, 1.0 mL from the inoculated test product was taken and placed into 9.0 mL of Modified Letheen Broth (1:10 dilution). Additional 1:10 serial dilutions were prepared using neutralizing broth to achieve 1:100 and 1:1000 dilutions.

1 mL from each dilution was plated in sterile Petri dishes, and melted TSA agar was added as the growth medium for bacterial organisms.

The bacterial plates were incubated at 30° C. to 35° C. for 48 hours. The same procedure was repeated for the Serological Saline Solution control. After the incubation period. All plates were counted to determine the number of microorganisms remaining at the various time points.

Results:

| Exposure Time | Concentration of Organism (CFU/mL) | | % Reduction | | Log Reduction | |
|---|---|---|---|---|---|---|
| | Control | Product | Control | Product | Control | Product |
| INITIAL | $1.80 \times 10^6$ | | | | | |
| 30 sec | $1.80 \times 10^6$ | $7.00 \times 10^4$ cfu/gm/ml | N/A | 96.11% | 0.00 | 1.41 |
| 1 min | $1.80 \times 10^6$ | $1.10 \times 104$ cfu/gm/ml | N/A | 99.38% | 0.00 | 2.21 |
| 5 min | $1.80 \times 10^6$ | <10 cfu/gm/ml | N/A | 99.99% | 0.00 | N/A |
| 30 min | $1.80 \times 10^6$ | <10 cfu/gm/ml | N/A | 99.99% | 0.00 | N/A |
| 60 min | $3.20 \times 10^5$ | <10 cfu/gm/ml | 82.22% | 99.99% | 0.75 | N/A |

Data Calculation was performed the same way as described above in Example 1.

Discussion: The minimum bactericidal concentration is defined as 99.99% decrease (3 log) in the initial inoculums. The test product had no counts for growth when exposed to *Staphylococcus aureus* after 5 minutes.

Conclusion: The results indicate that the test product has 99.9% log reduction for *Staphylococcus aureus* at 5 minutes of contact time.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A therapeutic extract for selectively treating bacterial skin disorders, the therapeutic extract comprising:
   about 15 to about 40 wt % glycerin;
   about 20 to about 30 wt % water;
   about 10 to about 30 wt % blackcurrant;
   about 10 to about 30 wt % pine;
   about 0.10 to about 1.00 wt % gluconolactone;
   about 0.10 to about 0.50 wt % citric acid; and
   about 0.10 to about 0.20 wt % sodium benzoate.

2. The therapeutic extract of claim 1, wherein the blackcurrant comprises organic ribes nigrum and is derived from fruit of a blackcurrant plant.

3. The therapeutic extract of claim 1, wherein the pine comprises *pinus* spp and is derived from a needle of a pine plant.

4. The therapeutic extract of claim 1, wherein the therapeutic extract comprises:
   about 30 wt % glycerin;
   about 29.2 wt % water;
   about 20 wt % blackcurrant;
   about 20 wt % pine;
   about 0.45 wt % gluconolactone;
   about 0.2 wt % citric acid; and
   about 0.15 wt % sodium benzoate.

5. The therapeutic extract of claim 1, wherein the extract comprises an equal amount of blackcurrant and pine.

6. A method of producing a therapeutic extract for selectively treating skin disorders, the method comprising:
   preparing dry botanicals;
   preparing an extraction solvent;
   extracting blackcurrant and pine;
   creating the therapeutic extract;
   pasteurizing the therapeutic extract;
   preserving the therapeutic extract; and
   optionally, packaging the therapeutic extract,
   wherein, the therapeutic extract comprises:
   about 15 to about 40 wt % glycerin;
   about 20 to about 30 wt % water;
   about 10 to about 30 wt % blackcurrant;
   about 10 to about 30 wt % pine;
   about 0.10 to about 1.00 wt % gluconolactone;
   about 0.10 to about 0.50 wt % citric acid; and
   about 0.10 to about 0.20 wt % sodium benzoate.

7. The method of claim 6, wherein preparing the dry botanicals comprises:
   obtaining dry herbs in whole form, wherein the dry herbs comprise the blackcurrant and the pint;
   dividing the dry herbs into a first half and a second half;
   putting the first half through a high-speed electric grinder mill at a speed of about 32000 r/min, to produce a dry rough mix;
   placing the dry rough mix and the second half into a mixing vessel; and
   blending the dry rough mix and the second half for about 15 minutes.

8. The method of claim 7, wherein preparing the extraction solvent comprises:
   mixing reverse osmosis water with aloe vera juice in a second mixing vessel for about 10 minutes;
   adding glycerin to the second mixing vessel and mixing for an additional 10 minutes, creating the extraction solvent.

9. The method of claim 8, wherein extracting the blackcurrant and the pine comprises:

introducing the extraction solvent into the mixing vessel, completely covering the dry mix;

closing the mixing vessel and leaving the mixing vessel closed for about 48 hours, creating an extract;

squeezing the extract through a heavy mechanical press, removing substantially all liquid matter; and filtering the liquid matter down to about 0.2 microns, helping to remove pathogens and particle matter, leaving a substantially clear, light pink liquid extract.

10. The method of claim 9, wherein pasteurizing the therapeutic extract comprises heating the substantially clear, light pink liquid extract to about 80 degrees for about 10 minutes to remove any remaining pathogens, creating a pasteurized extract.

11. The method of claim 10, wherein preserving the therapeutic extract comprises:

adding gluconolactone and sodium benzoate to the pasteurized extract; and adjusting a pH level of the pasteurized extract to be within a range of from about 4.6 to about 5, creating the therapeutic extract.

* * * * *